(12) United States Patent
Edwards et al.

(10) Patent No.: US 8,317,795 B2
(45) Date of Patent: Nov. 27, 2012

(54) SYSTEM AND METHOD OF BONE COMPRESSION AND FIXATION

(75) Inventors: Scott G. Edwards, McLean, VA (US); Ronald Yapp, Manchester, MI (US)

(73) Assignee: Scott G. Edwards, McLean, VA (US)

( * ) Notice: Subject to any disclaimer, the term of this patent is extended or adjusted under 35 U.S.C. 154(b) by 1465 days.

(21) Appl. No.: 11/859,009

(22) Filed: Sep. 21, 2007

(65) Prior Publication Data

US 2008/0077154 A1 Mar. 27, 2008

Related U.S. Application Data

(60) Provisional application No. 60/846,100, filed on Sep. 21, 2006.

(51) Int. Cl.
*A61F 2/46* (2006.01)
(52) U.S. Cl. .................................................. 606/86 R
(58) Field of Classification Search ............ 606/74, 606/86 R, 217, 232, 324
See application file for complete search history.

(56) References Cited

U.S. PATENT DOCUMENTS

| | | | |
|---|---|---|---|
| 4,409,974 A | 10/1983 | Freedland | |
| 4,741,330 A | 5/1988 | Hayhurst | |
| 5,306,290 A | 4/1994 | Martins et al. | |
| 5,370,646 A | 12/1994 | Reese et al. | |
| 5,810,848 A * | 9/1998 | Hayhurst | 606/144 |
| 5,893,850 A | 4/1999 | Cachia | |
| 5,921,986 A | 7/1999 | Bonutti | |
| 6,045,551 A | 4/2000 | Bonutti | |
| 6,068,648 A | 5/2000 | Cole et al. | |
| 6,102,934 A * | 8/2000 | Li | 606/232 |
| 6,117,160 A | 9/2000 | Bonutti | |
| 6,228,096 B1 * | 5/2001 | Marchand | 606/139 |
| 6,238,395 B1 | 5/2001 | Bonutti | |
| 6,368,326 B1 | 4/2002 | Dakin et al. | |
| 6,402,757 B1 * | 6/2002 | Moore et al. | 606/80 |
| 6,544,267 B1 | 4/2003 | Cole et al. | |
| 6,761,722 B2 | 7/2004 | Cole et al. | |
| 7,273,481 B2 | 9/2007 | Dakin et al. | |
| 2002/0188297 A1 | 12/2002 | Dakin et al. | |
| 2004/0010257 A1 | 1/2004 | Cachia et al. | |
| 2004/0044364 A1 | 3/2004 | DeVries et al. | |
| 2004/0097939 A1 | 5/2004 | Bonutti | |
| 2004/0127907 A1 | 7/2004 | Dakin et al. | |
| 2005/0033366 A1 | 2/2005 | Cole et al. | |
| 2006/0229623 A1 | 10/2006 | Bonutti et al. | |

OTHER PUBLICATIONS

International Search Report for PCT/US2007/079124 completed on Mar. 20, 2008.

* cited by examiner

*Primary Examiner* — Kevin T Truong
*Assistant Examiner* — Michael Araj
(74) *Attorney, Agent, or Firm* — Alston & Bird LLP

(57) ABSTRACT

A tension member installation and tensioning device and method for stabilizing a bone are provided. The device includes a barrel that houses a tension member with a leading element attached to the leading end of the tension member. The barrel of the device is inserted into a hole drilled through a bone until the barrel is beyond the distal cortex of the bone. The leading element is then engaged with the distal cortex. The leading element may be released from within the barrel or otherwise expanded to engage the distal cortex. The barrel is then retracted from the hole, and tension is applied to the tension member via a tensioning mechanism to attach a terminal element to a trailing portion of the tension member when a predetermined tension is achieved. The device may include a trigger for actuating the tensioning mechanism and a cutter for severing the tension member.

23 Claims, 13 Drawing Sheets

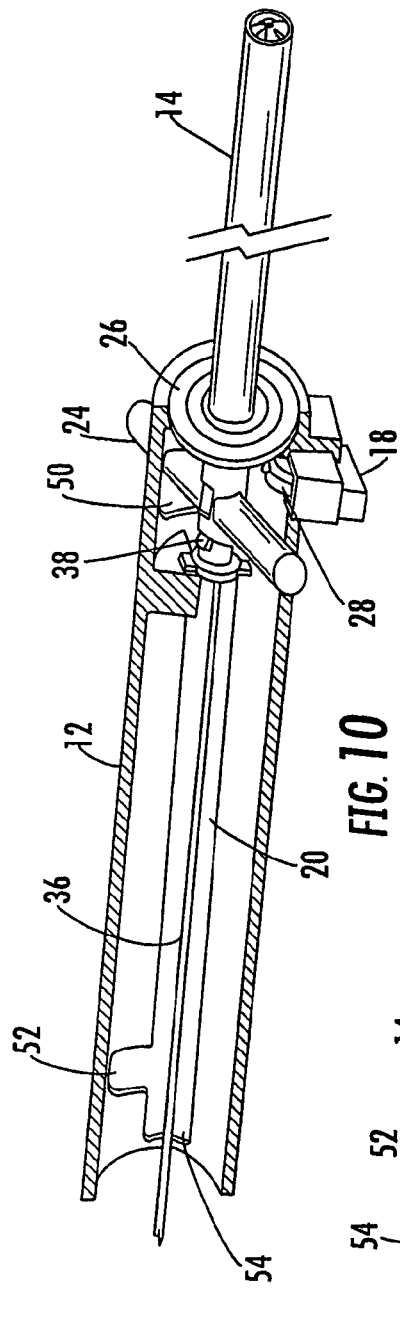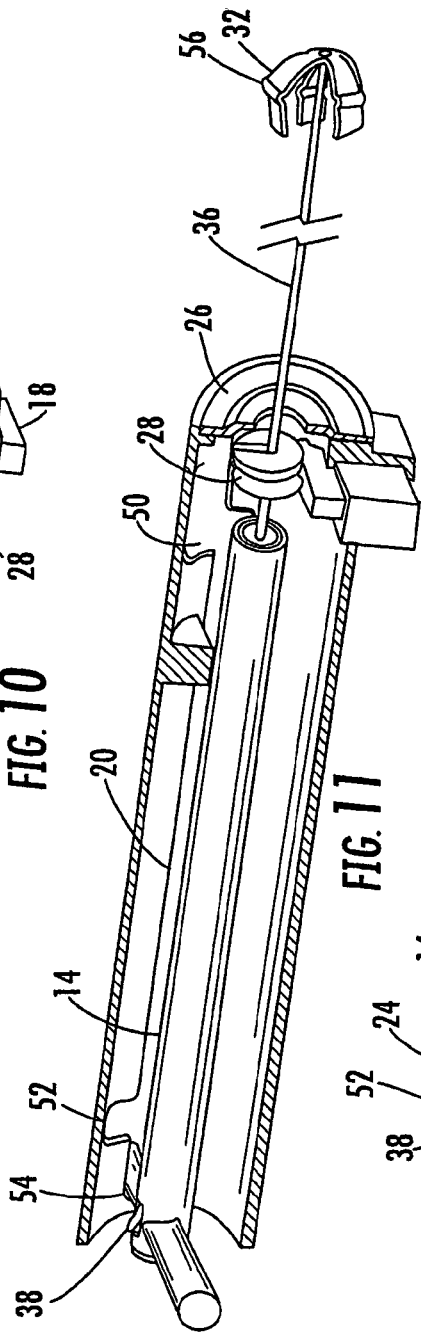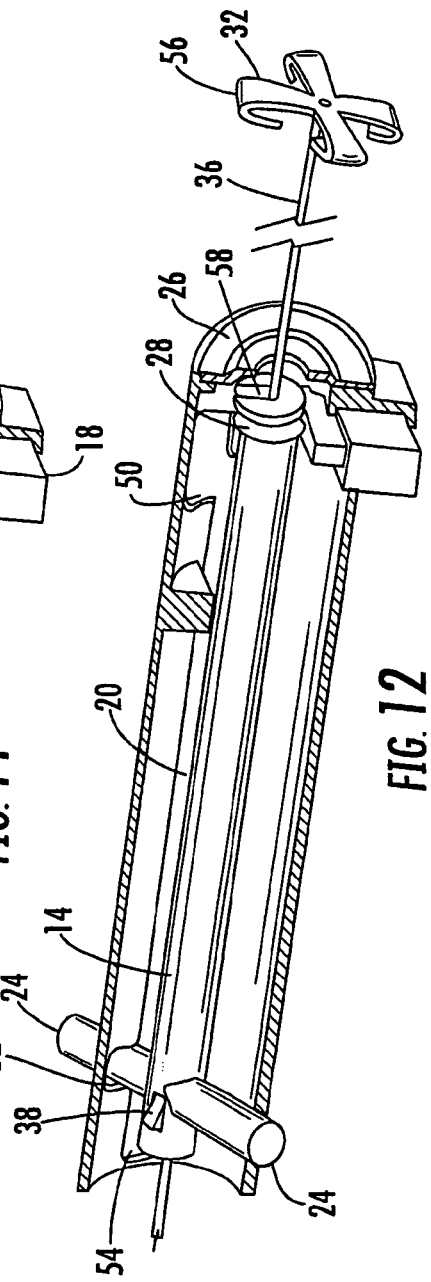

SYSTEM AND METHOD OF BONE COMPRESSION AND FIXATION

CROSS-REFERENCE TO RELATED APPLICATIONS

This application claims the benefit of U.S. Provisional Application No. 60/846,100, filed Sep. 21, 2006, which is hereby incorporated by reference.

FIELD OF THE INVENTION

The present invention relates to devices for installing a tension member in a bone and, more specifically, to a tension member application device for providing compression and stabilization of a bone.

BACKGROUND OF THE INVENTION

For years bones have been repaired using medical hardware such as nails, screws, or pins, often in combination with plates or rods. In order to stabilize a fractured bone, for example, the surgeon usually inserts one or more pieces of hardware across the fracture to hold the broken bones together in compression during the healing process. Compression is crucial to bone healing as it stabilizes the bone and stimulates bone growth. These hardware devices are often used in multiples because the compression force of the hardware is limited by how well the chosen hardware affixes to the bone. When more than one hardware device is used, they are often applied to opposing sides of the fracture requiring larger incisions or multiple incisions. The increase in the number of pieces of hardware also leads to increased time in surgery, higher cost of the surgery, greater potential for scarring and stiffness, and increased risk for another surgery to remove painful hardware.

When a person ages, their bones become more brittle as the cortex gets thinner, increasing the likelihood of broken bones. While weakened bones are prevalent in the elderly, such conditions are not limited to the elderly and can be found in people of any age. In weakened bones, the hardware used to repair a bone can cause damage to the bone when initially inserted and can more easily loosen from the bone during routine activity. With more brittle bones, hardware must be inserted more strategically in only the strongest parts of the bone, necessitating a maximum amount of holding force with a minimum amount of hardware. The problem then exists that if holding force is increased, or even remains constant, while using less hardware, the pressure exerted by each piece of hardware is increased in bone that likely cannot sustain the higher forces involved.

Thus, the need exists for a device to stabilize a bone that can be quickly and easily installed with minimal invasiveness. This device must be able to provide adequate holding force to facilitate healing, while reducing the risk of further damage to the bone. Advantageously, the device would also reduce human error by limiting the force that can be applied during installation.

BRIEF SUMMARY OF THE INVENTION

The present invention generally relates to a tension member installation and tensioning device for repairing bone. The device may be used to repair bone fractures, osteotomies, and other bone defects. Advantageously, in one embodiment, the device includes a barrel that houses a tension member, such as a cable, with a leading element attached to the leading end of the tension member. The barrel of the device is inserted into a hole drilled through a bone until the barrel is beyond the distal cortex of the bone. The leading element is then engaged with the distal cortex. The barrel is then retracted from the hole, and tension is applied to the tension member via a tensioning mechanism, such as a trigger, to attach a terminal element to a trailing portion of the tension member when a certain tension is achieved. Thus, the device may be used to install a tension member at a predetermined tension across a bone defect to promote healing without the need for multiple incisions or numerous pieces of hardware.

In one embodiment, the device includes a barrel configured to be inserted in a hole drilled bicortically through the bone and a tension member housed at least partially within the barrel and having a leading end. A leading element is attached to the leading end of the tension member, and the leading element is configured to pass through the hole and to engage a distal cortex of the bone. A terminal element is configured to attach to a trailing portion of the tension member and to engage a proximal cortex of the bone. The device also includes a tensioning mechanism configured to apply tension to the tension member, such that the terminal element attaches to the tension member at a predetermined tension of the tension member. In this way, a length of the tension member extending between the leading element and the terminal element may apply compression to the bone.

In some cases, the barrel includes an outer chamber and an inner chamber, where the outer chamber at least partially surrounds the inner chamber and the outer chamber is configured to slide over and lock onto the inner chamber, thereby releasing the leading element from the barrel. The leading element may include a body and a number of wings attached to the body, with the wings having a first position in which the wings are collapsed to allow the leading element to fit within the outer chamber and a second position in which the wings are expanded to increase a width of the leading element and permit engagement with the distal cortex. In some embodiments, the wings are configured to be generally perpendicular to the tension member when in the second position and are configured to move from the first position to the second position when unrestrained by the outer chamber.

In other cases, the leading element includes a distal end, a proximal end, and at least one flat member connecting the distal and proximal ends. Each flat member may be configured to bend outward and expand a width of the leading element to engage the distal cortex when the distal end is drawn toward the proximal end via the tension member.

In some embodiments, the device includes a casing at least partially housing the barrel and configured to allow the barrel to move longitudinally within the casing. Thus, the terminal element may include a static washer removably attached to an end of the casing and a crimp. The static washer may be configured to receive the crimp, and the crimp may be configured to attach to the tension member and to engage the static washer. The static washer and crimp may be configured with a taper, and the crimp may be configured to collapse around the tension member when axially loaded under tension via the tension member. In some cases, the crimp may define a slot extending from an edge of the crimp towards a center of the crimp, and the slot may be configured to receive the tension member. The crimp may be configured to deform to attach to the tension member, and/or the crimp may include a scoring edge configured to score the tension member.

Furthermore, the tensioning mechanism may include a trigger configured to apply tension to the tension member. The tensioning mechanism may further include at least one gear configured to interact with the trigger and the tension member and to apply tension to the tension member upon actuation of the trigger. In some cases, the terminal element includes a cutter configured to cut the tension member near the terminal element such that the length of the tension member extending between the leading element and the terminal element is detached from the device.

In other embodiments, a method of installing a tension member for stabilizing a bone is provided. A barrel is initially inserted into a hole drilled in the bone such that an end of the barrel extends beyond a distal cortex of the bone. The barrel at least partially houses the tension member, and a leading element is attached to a leading end of the tension member. The leading element is then engaged with the distal cortex, and the barrel is withdrawn from the hole. Tension is then applied to the tension member to attach a terminal element to a trailing portion of the tension member, where the terminal element is configured to attach to the tension member and engage a proximal cortex of the bone when a predetermined amount of tension on the tension member is achieved.

In some cases, an outer chamber of the barrel is moved over an inner chamber of the barrel such that the outer chamber releases the leading element and locks onto the inner chamber. Tension may be applied to the tension member to draw a distal end of the leading element toward a proximal end of the leading element, thereby expanding the leading element. A crimp may thus be applied to the trailing portion of the tension member when the predetermined amount of tension is achieved, where the crimp is configured to engage a static washer to form the terminal element. The crimp may be deformed when the predetermined amount of tension is achieved to attach the crimp to the tension member.

In some embodiments, a trigger may be actuated to incrementally increase the tension in the tension member. The tension member may also be cut proximate the terminal element, which, in some cases, may be done by deforming at least part of the terminal element to score the tension member and applying force to the tension member to sever the tension member.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 10 is a section view of the tension member application device as inserted into a hole spanning the fracture according to one embodiment;

FIG. 11 is a section view of the tension member application device after retraction of the barrel into the casing according to one embodiment;

FIG. 12 is a section view of the tension member application device upon locking the barrel in the casing and tensioning the tension member according to one embodiment;

DETAILED DESCRIPTION OF THE DRAWINGS

Figure 1:
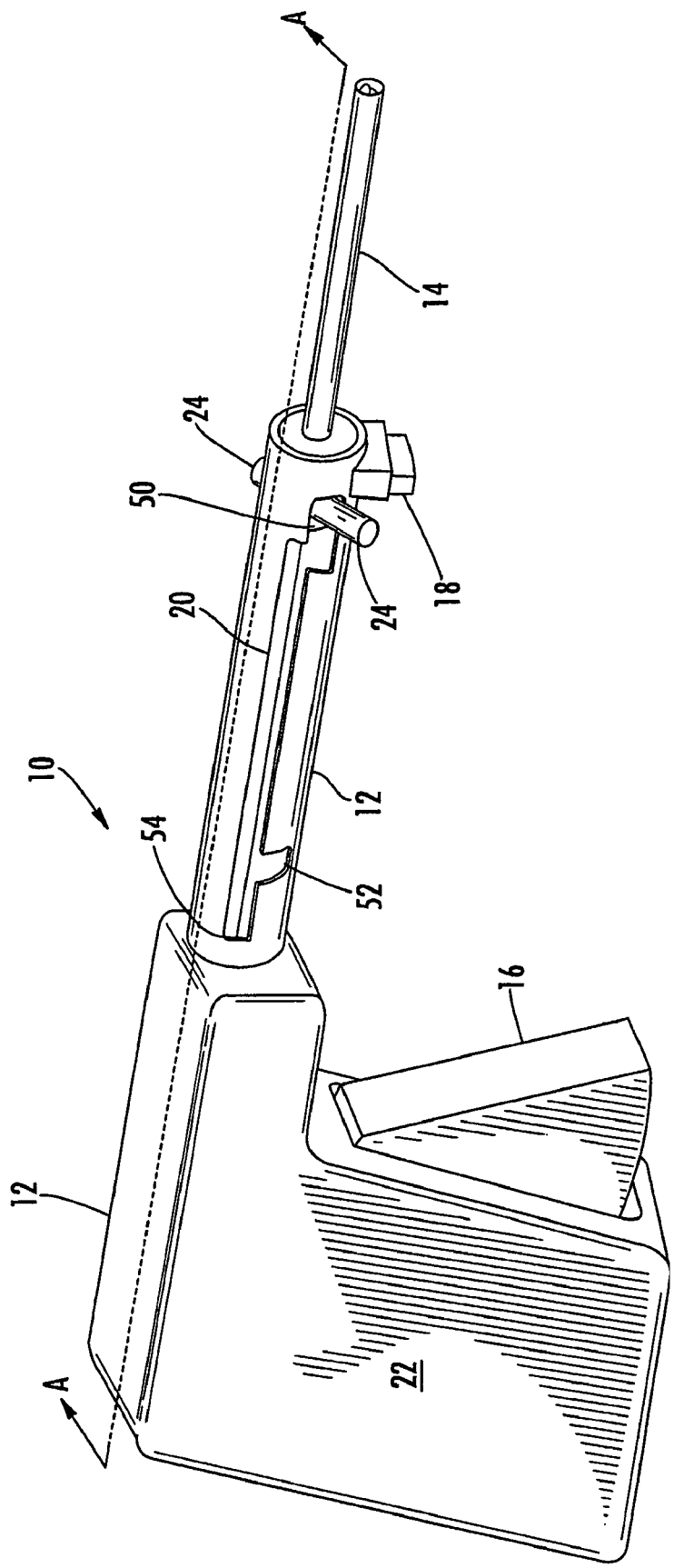
FIG. 1 is an isometric view of the tension member application device according to one embodiment.

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Embodiments of the present invention generally relate to a tension member installation and tensioning device for repairing bone. For example, the device may be used to repair bone fractures, osteotomies, and other bone defects. For ease of explanation, however, the specification and accompanying figures will refer to bone fractures, although it is to be understood that any type of bone repair, including the repair of fractures, osteotomies, and other bone defects, may be accomplished using embodiments of the device described herein.

As described further below, the tension member application device includes a barrel that houses a tension member with a leading element attached to the leading end of the tension member. In general, the barrel of the tension member application device is inserted into a hole drilled bicortically through a bone until the barrel is beyond the distal side of the hole. The leading element is released from the barrel or otherwise deployed to engage the distal cortex of the bone. The barrel is then retracted from the bone, and a terminal element is attached to a trailing portion of the tension member. A tensioning mechanism is used to apply tension to the tension member, and at a predetermined tension the terminal element attaches to the tension member and engages the proximal cortex of the bone. In some cases, a crimp surrounds the tension member and engages a static washer to form the terminal element. The crimp may either be pushed onto the tension member, or it may be pre-threaded on the tension member, such as during manufacture of the tension member application device. The device may further include a trigger or any other form of control for applying tension to the tension member (e.g., a button or switch) and a cutter for severing the tension member from the application device after installation.

The tension applied to the tension member (i.e., the predetermined tension) necessarily varies based on several factors of each individual operation. For example, the size, type, and condition of the bone, the configuration and material type of the leading and terminal elements, and numerous other factors contribute to determine the appropriate tension that is applied to the tension member for attaching the terminal element and stabilizing the bone. In some embodiments, typical ranges of tension that may be applied are between about 5 and 50 pounds-force. For example, when stabilizing a young healthy bone during a procedure for repairing a proximal tibia periarticular fracture, the predetermined tension may be around 30 pounds-force. Furthermore, the necessary tension may dictate the material type and size of the tension member.

Referring to FIG. 1, a tension member application device 10 according to one embodiment is shown in the isometric view. The device 10 of FIG. 1 includes a casing 12, a barrel 14, and a trigger 16. The casing 12 and barrel 14 may, for example, be made of high-grade plastic, metal, or other material suitable to a sterile surgical environment. The barrel 14 is configured (i.e., sized and shaped) to be inserted into a hole 15 drilled through a fractured bone 17 (shown in FIG. 2A); thus, the particular configuration of the barrel 14 may vary depending on the type and size of the bone to be treated. For example, a barrel 14 to be used for fixing a fracture of an adult femur may have different dimensions than a barrel 14 to be used for fixing a fracture of a child's humerus.

The barrel 14 may be configured to fit within and be movable through at least part of the casing 12. For example, as depicted in FIG. 1, the casing 12 may include one or more slots 20 through which one or more barrel handles 24 may extend to facilitate the movement of the barrel 14 through the casing 12. In this way, the barrel handles 24 may be moved along the slots 20 towards a grip portion 22 of the casing 12 such that the barrel 14 may be retracted into the casing 12, as described below.

Figure 1A:
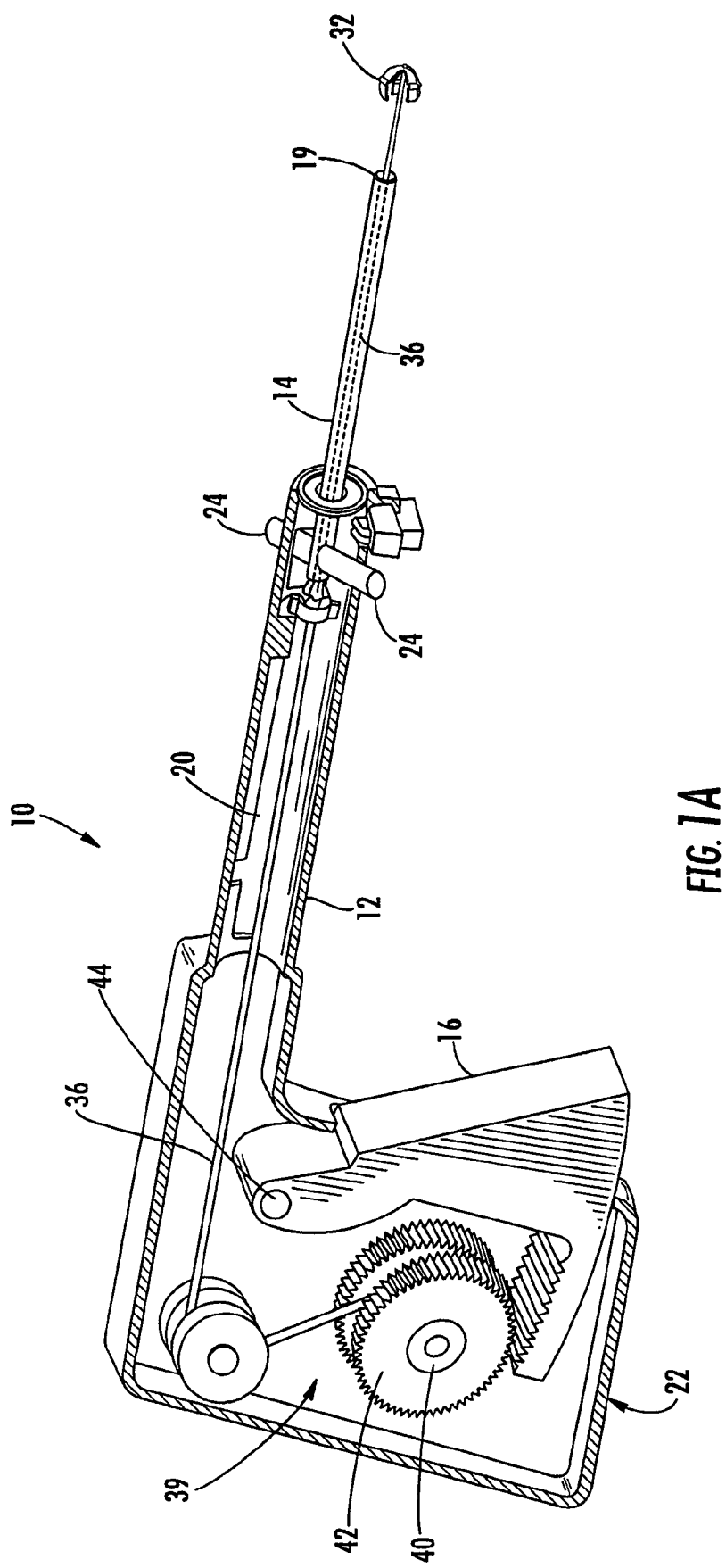
FIG. 1A is a section view of the isometric view of the tension member application device of FIG. 1.

FIG. 1A shows the inside of the casing 12 of the tension member application device 10 depicted in FIG. 1, including a tensioning mechanism 39 (described below). A tension member 36 with a leading end 19 is housed at least partially within the barrel 14 and is attached at the leading end 19 to a leading element 32. The leading element 32 may be made of a material such as stainless steel, titanium, shape memory alloy, polymer or other materials suitable for use within the human body. The tension member 36 may be made of a material such as braided or non-braided stainless steel, titanium, polymer or other material suitable for use within the human body, or a combination of such materials. In some cases, the tension member 36 may be a two-section member including a more rigid portion of the tension member 36 that is inserted into the fractured bone, and a second portion of more flexible material for the section of the tension member 36 that engages the tensioning mechanism 39. These two materials may be joined such that the transition between the two materials does not affect the function of the tension member application device 10. For example, the tension member 36 may include a leading portion made of monofilament wire that is welded to a trailing portion made of braided stainless steel.

Figure 2A:
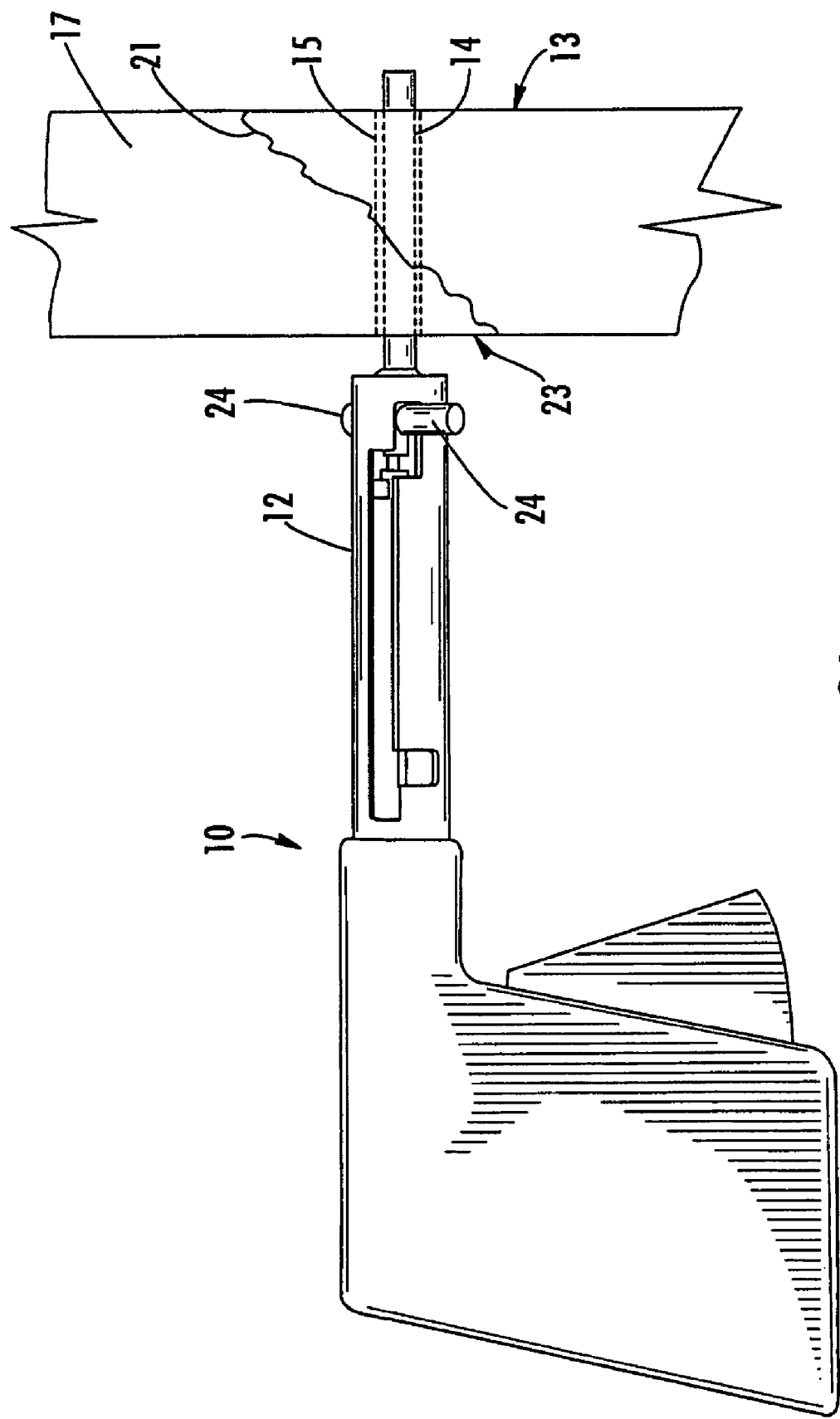
FIG. 2A is an illustration of the tension member application device inserted through a hole drilled in a fractured bone according to one embodiment.
Figure 2B:
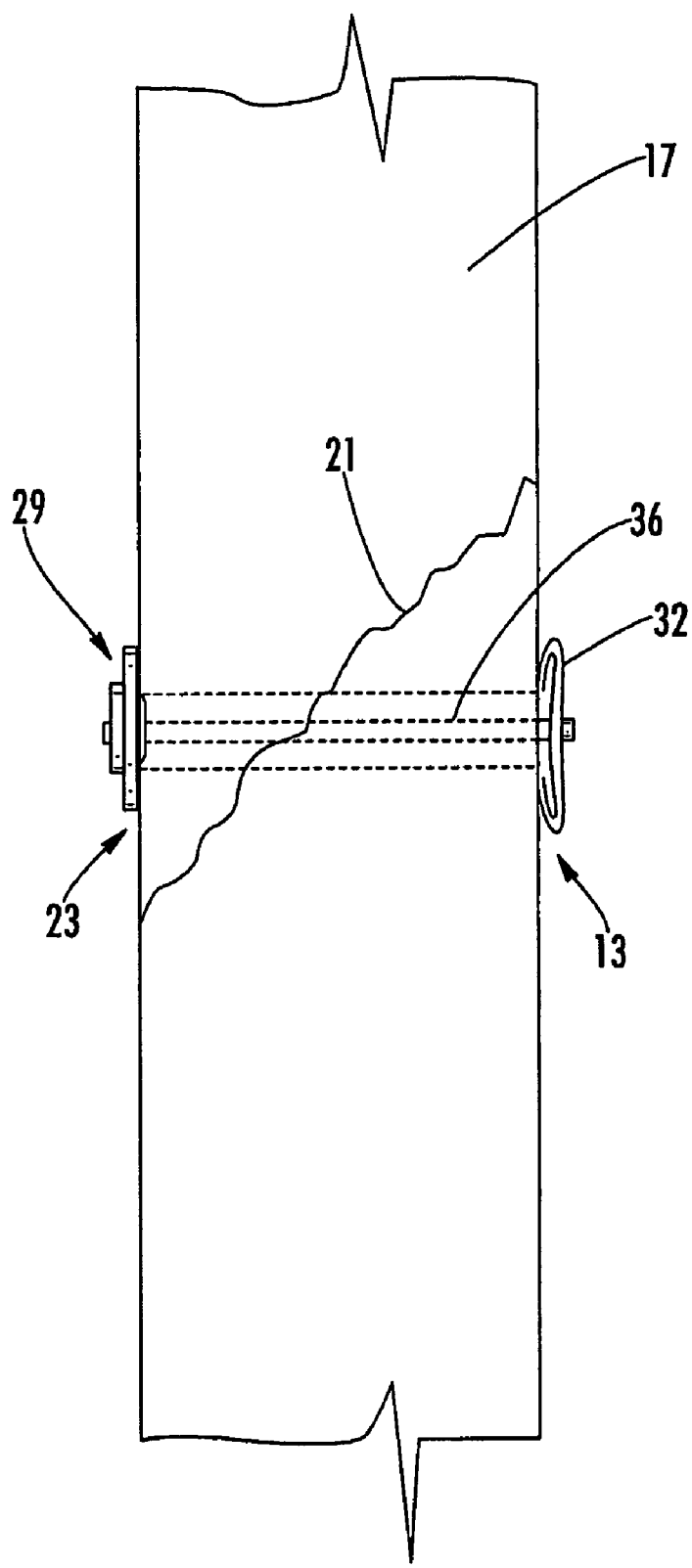
FIG. 2B is an illustration of the tensioned tension member spanning the fracture with a leading element and a terminal element affixed to the tension member according to one embodiment.

The tension member 36 may extend from the leading element 32, through the barrel 14 and the casing 12, and into the grip portion 22 of the casing 12, where it may engage the tensioning mechanism 39. Referring to FIGS. 1A and 2B, the leading element 32 (shown released from the barrel 14 in FIG. 1A) is configured to expand according to one embodiment so as to engage a distal cortex 13 of the bone 17 on a distal side of the fracture 21 (as shown in FIG. 2B). It should be noted that although FIGS. 2A and 2B show the tension member installation on a fracture across the shaft of the bone, the tension member application device 10 may be used to repair fractures of bones having other configurations, such as pelvic fractures, and periarticular fractures, i.e., fractures at the end of the bone near the location of a joint, where installation of plates and screws for fracture fixation could result in painful, prominent hardware or loss of fixation secondary to screws pulling away from the relatively soft bone. Furthermore, as previously mentioned, the tension member application device 10 may be used to repair osteotomies and other bone defects not illustrated.

Figure 3:
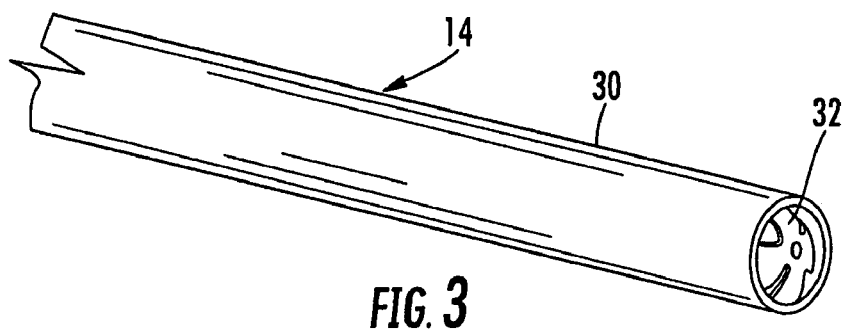
FIG. 3 is an illustration of an expandable leading element confined within an outer chamber of the tension member application device according to one embodiment.
Figure 4:
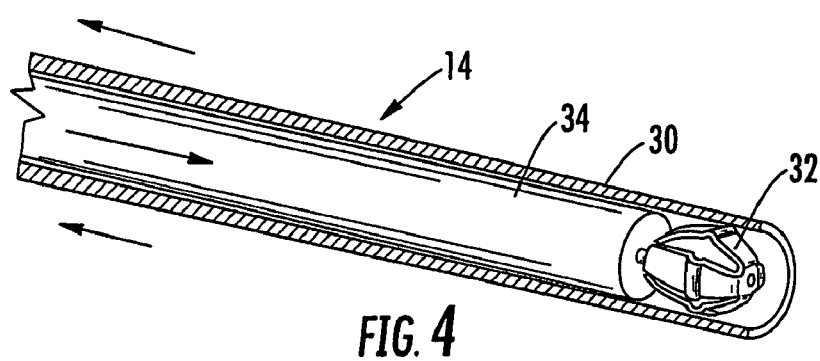
FIG. 4 is a section view of the outer chamber of FIG. 3 showing an inner chamber and the leading element confined within the outer chamber.
Figure 5:
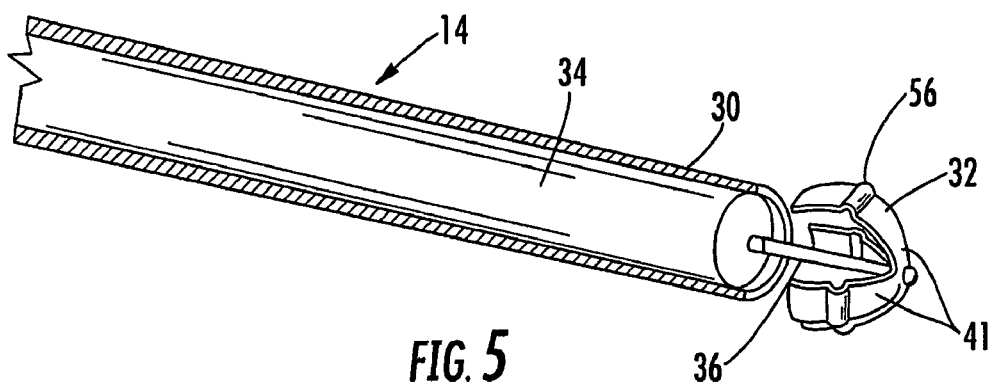
FIG. 5 is a section view of the outer chamber of FIG. 3 after the leading element has been pushed through the outer chamber by the inner chamber.

Referring to FIGS. 3-6, the barrel 14 may include an outer chamber 30 and an inner chamber 34. As seen in FIGS. 4 and 5, the outer chamber 30 may be configured to at least partially surround the inner chamber 34. Furthermore, the outer chamber 30 may be configured to slide over the inner chamber 34, such that the inner and outer chambers 34, 30 may be locked onto each other and may subsequently move in unison as the barrel 14, as further described below. For example, the inner and outer chambers 34, 30 may initially be configured as shown in FIGS. 3 and 4, with the leading element 32 disposed at a leading end of the inner chamber 34 and held in a collapsed position by the walls of the outer chamber 30. Another embodiment may eliminate the need for a separate inner chamber 34 by providing a leading element 32 that is held in place against a leading edge of the outer chamber 30 or barrel 14 via the tension member 36, as described below.

Once the barrel 14 of the tension member application device 10 is inserted into the hole 15 drilled through the fractured bone 17 (i.e., spanning the fracture) such that the end of the barrel 14 extends beyond the distal cortex 13 of the bone 17 (as shown in FIG. 2A), the leading element 32 may be released from the barrel 14 and allowed to expand. To release the leading element 32, the outer chamber 30 is pulled back with respect to the inner chamber 34 (the relative movement of the chambers 34, 30 being indicated by the arrows in FIG. 4), which locks the chambers 30, 34 together, thereby forcing the leading element 32 out of the outer chamber 30, as shown in FIG. 5, and permitting the leading element 32 to expand and engage the distal cortex.

Figure 6:
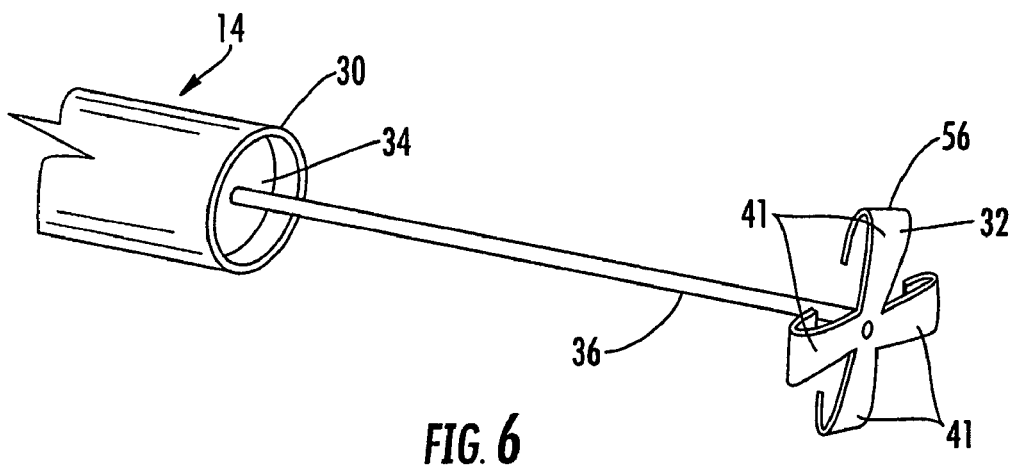
FIG. 6 is an illustration of the leading element of FIG. 3 when it is fully expanded according to one embodiment.
Figure 8:
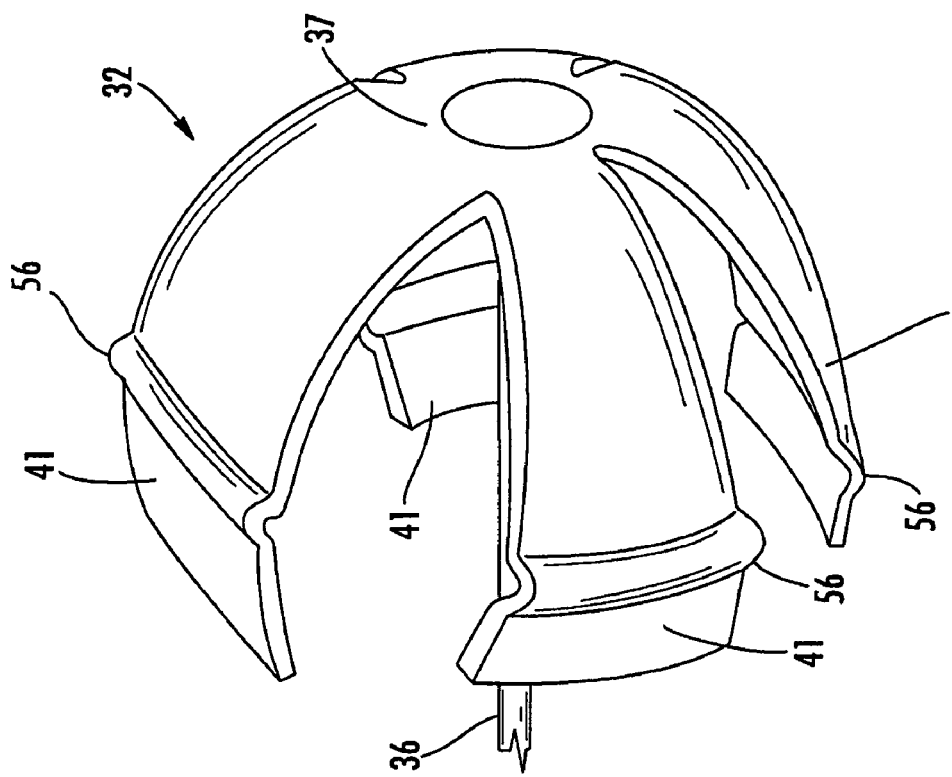
FIG. 8 is an illustration of the leading element with a living hinge according to another embodiment.
Figure 7:
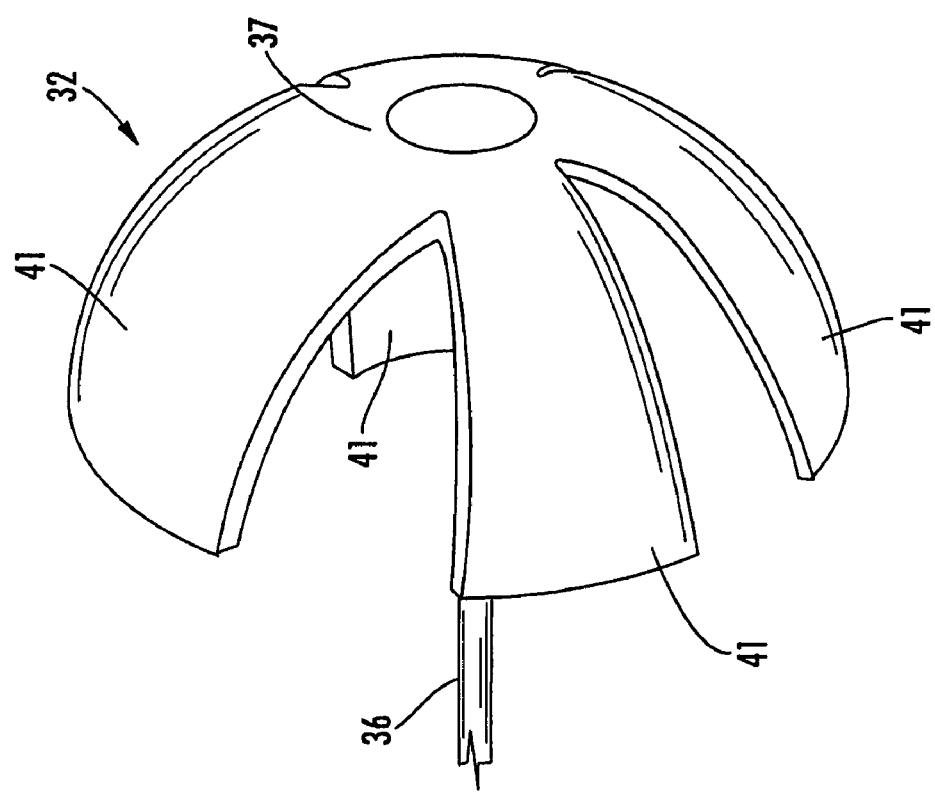
FIG. 7 is an illustration of the leading element according to one embodiment.

In this regard, the leading element 32 may include a body 37 and a number of wings 41 attached to the body, as illustrated in FIG. 7. The wings 41 may be configured to have a first position, in which the wings 41 are collapsed to allow the leading element 32 to fit at least partially within the outer chamber 30 (e.g., as shown in FIGS. 3 and 4) for passage through the hole, and a second position, in which the wings 41 are expanded to increase a width of the leading element 32 (e.g., as shown in FIGS. 5 and 6) and allow engagement of the distal cortex. For example, the wings 41 may be configured to be generally perpendicular to the tension member 36 (e.g., via a spring or other biasing mechanism) when in the second position such that, when unrestrained by the outer chamber 30, the wings 41 move from the first position to the second position. In another embodiment, shown in FIG. 8, the leading element 32 includes wings 41 that each comprise a living hinge 56. The living hinge 56 is configured such that in the expanded position, each wing 41 folds onto itself providing reinforcement to the leading element 32 (as shown in FIG. 6). When the tension member 36 is tensioned, as described below, the leading element 32 may be fully expanded, as shown in FIG. 6, to create a larger surface for engagement with the distal cortex 13 of the fractured bone 17 (as shown in FIG. 2B).

Figure 19A:
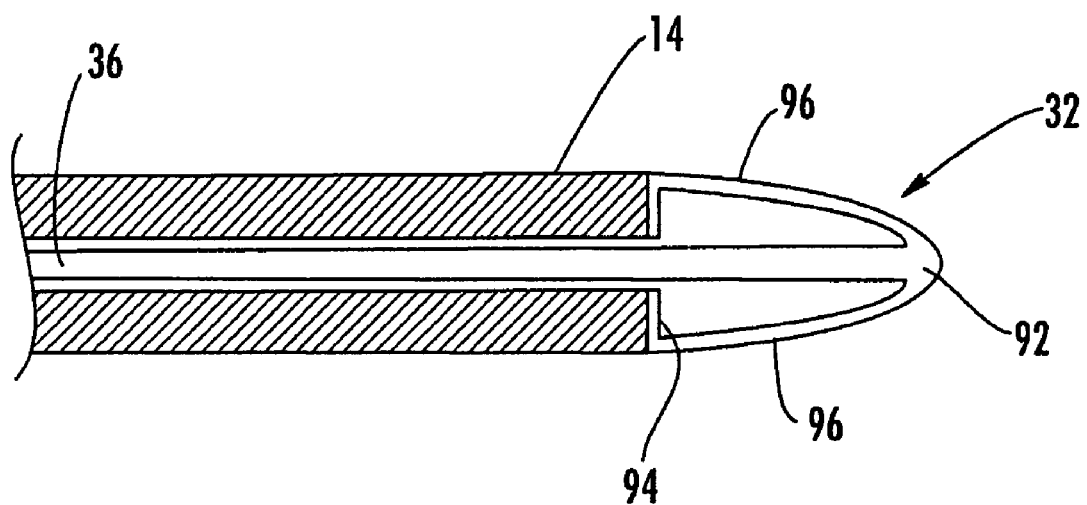
FIG. 19A is an illustration of a leading element before it is expanded according to one embodiment.
Figure 19B:
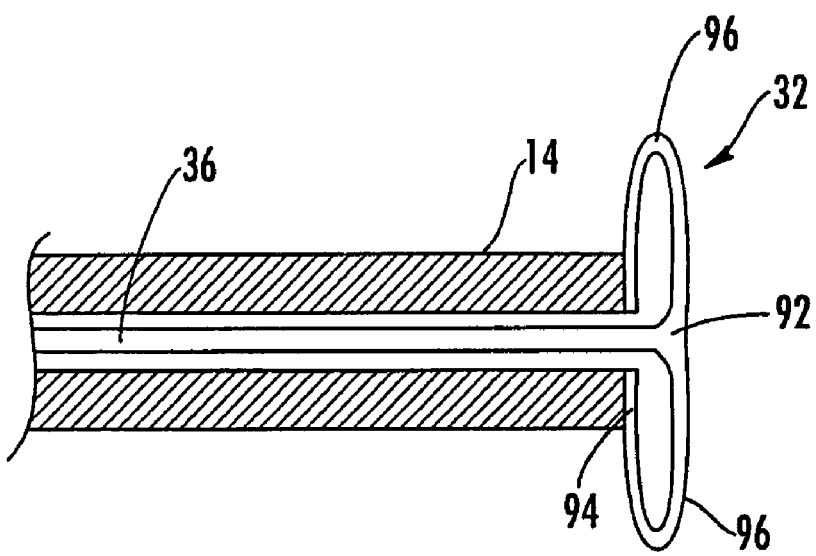
FIG. 19B is an illustration of a leading element of FIG. 19A after it is expanded.

Another embodiment of the leading element 32, shown in FIGS. 19A and 19B, may include a leading element 32 that is held outside the barrel 14 and has an initial diameter generally equal to the diameter of the barrel 14, but that includes one or more flat members 96 that are configured to expand when tension is applied to the tension member 36, thereby eliminating the need for separate inner and outer chambers. In this case, the tension member 36 is attached to the distal end 92 of the leading element 32 and the proximal end 94 of the leading element 32 is held in place against the barrel 14 via the tension member 36 (FIG. 19A). Once the leading element 32 is inserted beyond the distal cortex, tension may be increased in the tension member 36 such that the distal end 92 of the leading element 32 may be pulled towards the proximal end 94 of the leading element 32. As a result, the flat members 96 of the leading element 32 may bend outward and permanently deform to create a surface with an expanded diameter greater than that of the hole drilled through the bone, thereby allowing the leading element 32 to engage the distal cortex (FIG. 19B). In some cases, each flat member 96 may include a stress riser to facilitate bending of the flat member 96 in the area of the stress riser when tension is applied.

Figure 9:
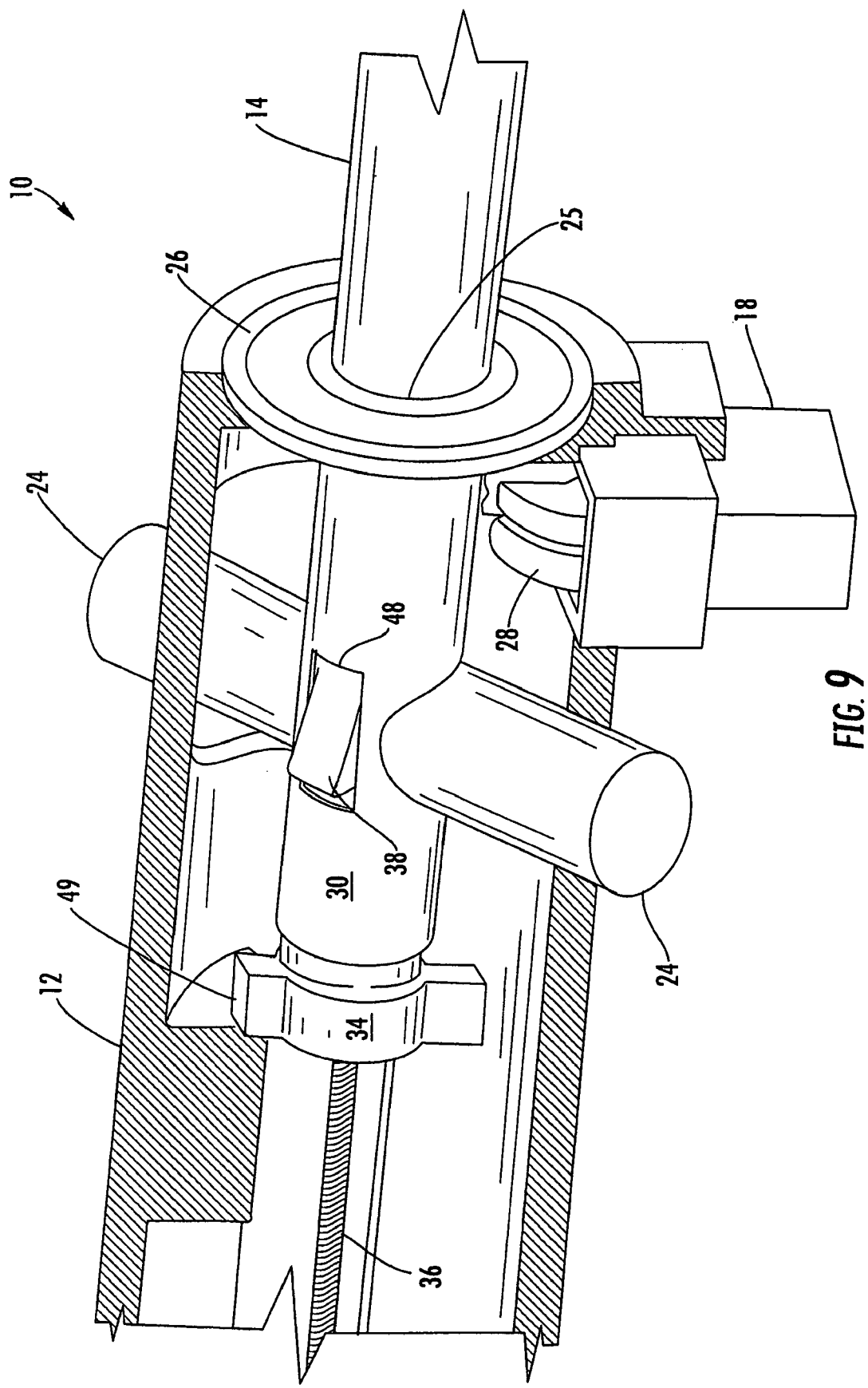
FIG. 9 is a section view of a casing of the tension member application device with a static washer attached to the casing according to one embodiment.

Referring to FIG. 9, in embodiments including an inner chamber 34 and an outer chamber 30 of the barrel 14, the outer chamber 30 may include an opening 48 configured to receive a tab 38 of the inner chamber 34. The tab 38 may be configured to allow the outer chamber 30 to slide over the tab 38 when being moved relative to the inner chamber 34 in the direction shown in FIG. 4. For example, the inner chamber 34 may include stops 49 configured to engage a portion of the casing 12 such that the inner chamber 34 may be held stationary as the outer chamber 30 is moved into locking engagement with the inner chamber 34. Once the tab 38 of the inner chamber 34 is received by the opening 48 of the outer chamber 30, the inner chamber 34 and outer chamber 30 together form the barrel 14 and may be moved in unison to complete installation of the tension member 36 in the fractured bone.

The tension member application device 10 further includes a terminal element 29 configured to attach to a trailing portion of the tension member 36 and to engage a proximal cortex 23 of the bone 17, as shown in FIG. 2B. Referring again to FIG. 9, the terminal element may include a static washer 26 and a crimp 28. The static washer 28 and crimp 26 may, for example, be composed of stainless steel, titanium, or other materials compatible with the human body, though they need not be composed of the same material. The static washer 26 may be removably attached to an end of the casing 12, such as via a press fit or interference fit, and the crimp 28 may be configured to attach to the tension member 36 and to engage the static washer 26. For example, the crimp 28 may be disposed in a crimp ejection mechanism 18 and may be positioned away from the barrel 14, such that the barrel 14 is permitted to move within the casing 12 without being hindered by the crimp 28. Alternatively, the crimp may be free from the device and added by the surgeon at some point during the procedure. The static washer 26 may be configured such that the barrel 14 is able to pass through a void 25 formed in a central portion of the static washer 26 without detaching the static washer 26 from the casing 12.

Turning to FIGS. 10-12, once the barrel 14 is installed in a hole spanning the fracture, the barrel 14, which is initially positioned such that the barrel handles 24 are in one or more first locking slots 50 extending from longitudinal slots 20, may be placed in a first locked position by moving the barrel handles 24 along the first locking slots 50 (towards the grip portion 22 shown in FIG. 1) in order to lock the inner and outer chambers 34, 30 and release the leading element 32 to engage the distal cortex, as previously described (FIG. 10). The barrel 14 may then be rotated from the first locking slots 50 into the longitudinal slots 20 and retracted into the casing 12, towards the grip portion 22 (shown in FIG. 1) as previously described, until the barrel handles 24 are at the ends 54 of the longitudinal slots 20 and the barrel 14 is clear of the crimp 28 (FIG. 11).

The crimp ejection mechanism 18 may be configured to move towards the barrel 14 and casing 12, such that, once the barrel 14 has been retracted into the casing 12 past the location of the crimp 28, for example, to the ends 54 of the longitudinal slots 20, the crimp ejection mechanism 18 may be moved towards the now exposed tension member 36, as shown in FIG. 11. The crimp ejection mechanism 18 may in some cases be manually movable, such that a surgeon may push on an external portion of the mechanism 18 to move it towards the tension member 36. In other cases, the crimp ejection mechanism 18 may be spring-loaded or otherwise biased such that the mechanism 18 automatically moves towards the tension member 36 once the barrel 14 is clear.

Figure 16:
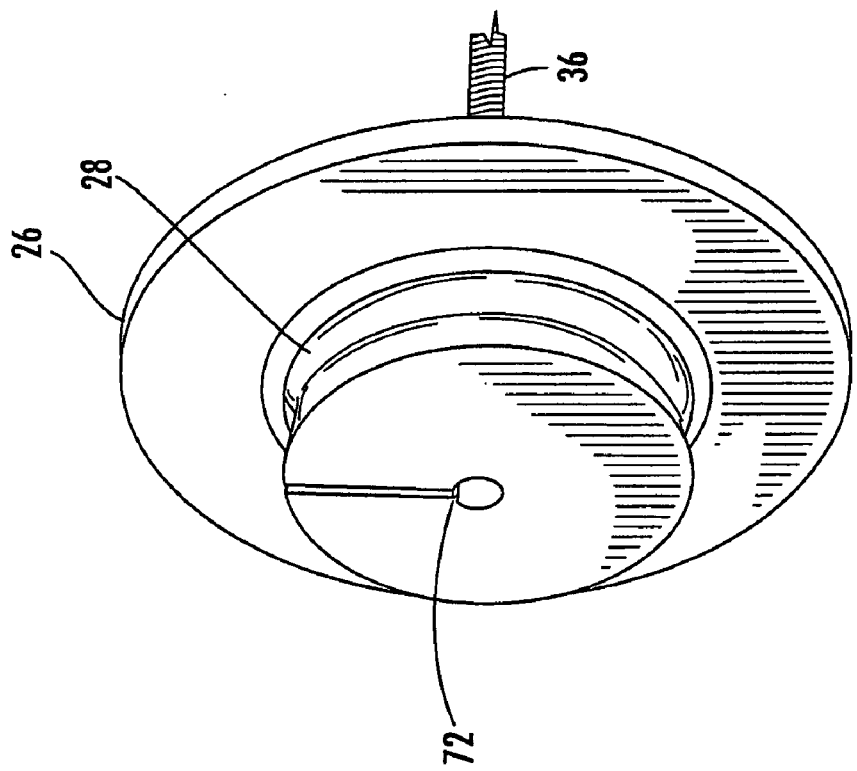
FIG. 16 is an illustration of the terminal element fastened into position with the tension member severed.
Figure 15:
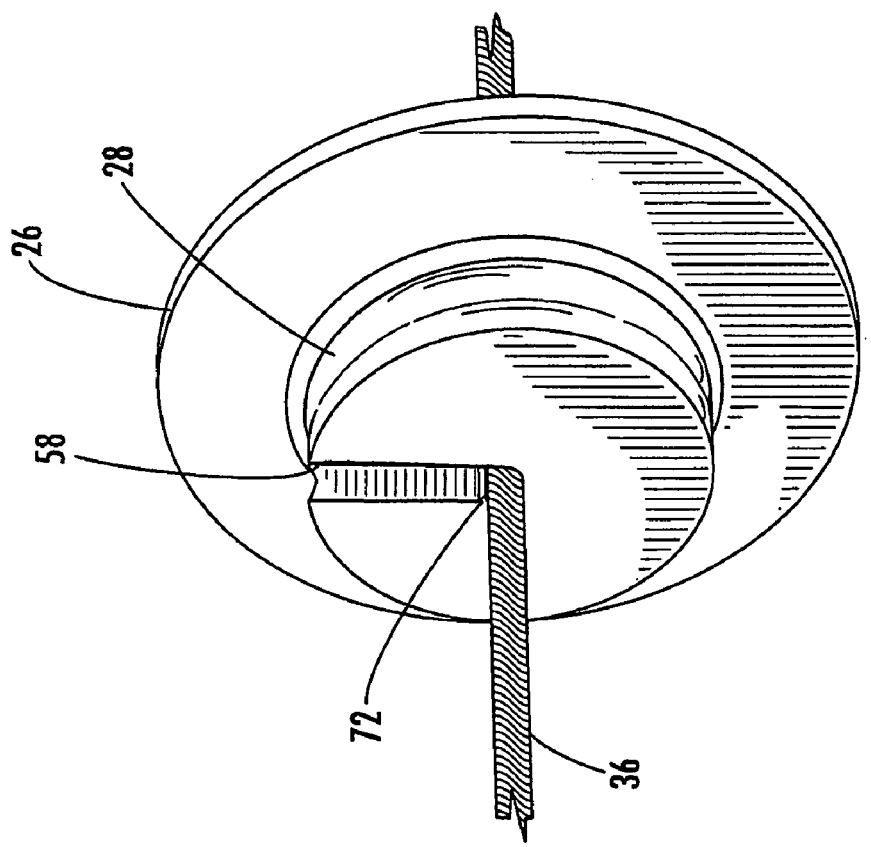
FIG. 15 is an illustration of a terminal element with a cutting edge for severing the tension member.

The crimp 28 may define a slot 58 extending from the edge of the crimp 28 towards the center of the crimp 28 (as shown in FIG. 12). In some cases, the slot may also extend past the center of the crimp. The slot 58 may thus be configured to receive the tension member 36, such that, once the crimp ejection mechanism 18 is moved towards the tension member 36, the tension member 36 may fit within the slot 58. The crimp 28 may be made of a material that deforms as a predetermined amount of force is applied to the crimp 28. In this way, the crimp 28 may be configured to deform to hold the tension member 36, for example, causing the slot 58 to surround and attach to the tension member 36 (as shown in FIGS. 15-16 and described below).

In some embodiments, the crimp 28 may be configured to automatically attach to the tension member 36 at a predetermined tension of the tension member 36. Thus, tension may be applied to the tension member 36, for example, via the tensioning mechanism 39 shown in FIGS. 1A, 13, and 14, and the crimp 28 may automatically attach to the tension member 36 once the tension in the tension member 36 reaches a certain level. Referring to FIG. 12, the barrel 14 may be moved into one or more second locking slots 52 extending transversely from the longitudinal slots 20 via rotation of the barrel handles 24 such that the leading end of the barrel 14 engages the crimp 28, which presses against the static washer 26, releasing it from the casing 12 and causing it to protrude beyond the end of the casing 12. As tension is applied to the tension member 36, the proximal cortex 23 of the bone 17 (shown in FIG. 2B) will press against the static washer 26, which will transmit the force to the engaged crimp 28. On the other side of the crimp 28, the end of the barrel 14 will apply an opposite force to the crimp 28, thereby "sandwiching" the crimp 28 between the barrel 14 on one side and the static washer 26 on the other. As the force approaches the value at which the crimp 28 is configured to deform (due to increasing tension applied to the tension member 36), the crimp 28 will attach to the tension member 36 as a result of deformation of the crimp 28 (e.g., the slot 58) around the tension member 36. In this embodiment, the crimp 28 and the static washer 26 may be configured to fit together, as shown in FIG. 15, so as to combine to form the terminal element 29 (shown in FIG. 2B), which will hold the tension in the tension member 36 once the tensioning operation is complete.

Figure 17:
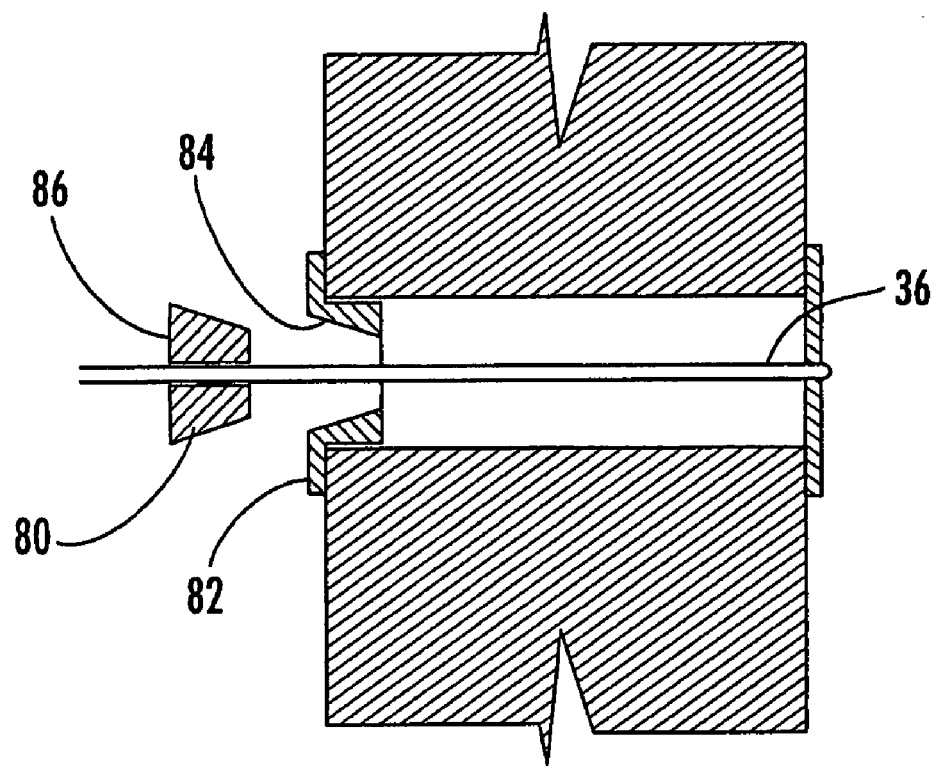
FIG. 17 is an illustration of the crimp and static washer of the terminal element according to another embodiment.
Figure 18:
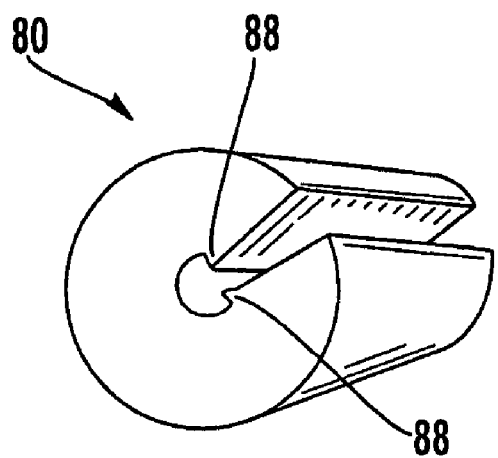
FIG. 18 is an illustration of the crimp of FIG. 17 showing a scoring edge according to one embodiment.

Referring to FIG. 17, another embodiment of a crimp 80 may include a static washer 82 with an internal taper 84. The crimp 80 may be configured such that when the barrel 14 of the tension member application device 10 applies force to the proximal side 86 of the crimp 80 via tensioning the tension member 36, the crimp 80 is forced into the taper 84 of the static washer 82, causing the crimp 80 to deform and attach to the tension member 36. The crimp 80 may further include one or more scoring edges 88 (shown in FIG. 18) configured to score or otherwise pierce the tension member 36 such that it is totally severed or can be easily severed from the tension member application device 10. For example, upon achieving the predetermined amount of tension in the tension member 36, the tension member 36 may be sufficiently scored such that the surgeon may manually sever the tension member 36 by twisting the tension member application device or otherwise applying force to the scored area.

Figure 13:
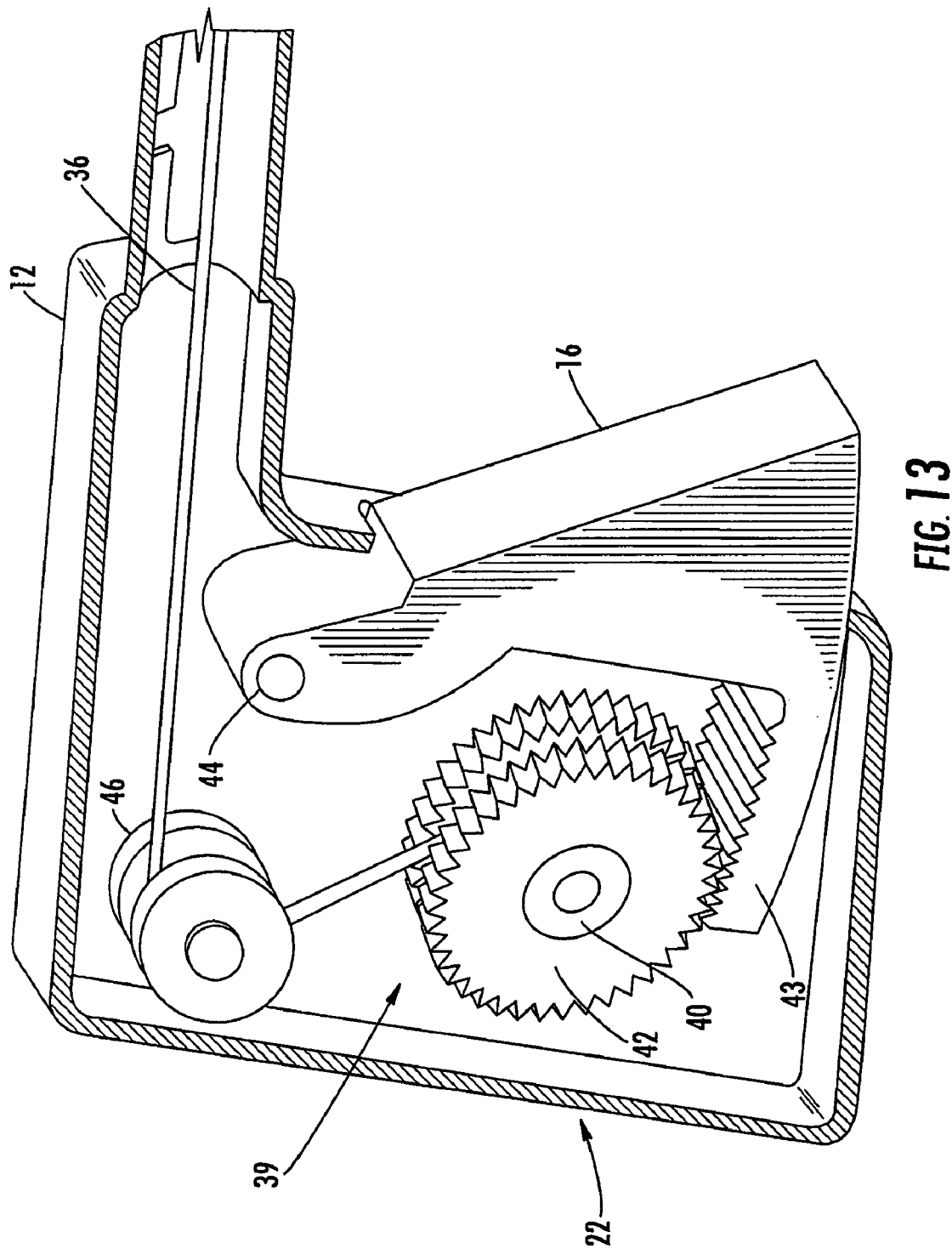
FIG. 13 is a section view of the casing and a grip portion of the tension member application device showing a tensioning mechanism according to one embodiment.

Referring to FIG. 13, the grip portion 22 of the tension member application device 10 is shown in a sectional isometric view that displays the tensioning mechanism 39 within the casing 12 according to one embodiment. In this embodiment, the tensioning mechanism 39 includes a hub 40, a gear 42, and a guide hub 46 to align the tension member 36 with the barrel 14. The tension member 36 is secured around the hub 40, which is mounted on a one-way-clutch (not shown) within the gear 42. The other end (i.e., the leading end) of the tension member 36 is attached to the leading element, as previously described. The trigger 16 is configured to apply tension to the tension member 36. For example, in the illustrated embodiment, actuation of the trigger 16 turns the gear 42 via engaging teeth 43, which in turn rotates the hub 40 and winds the tension member 36 around the hub 40. When the trigger 16 is released, the trigger 16 springs back to the extended position for subsequent actuation, for example, via a coiled spring or other biasing mechanism (not shown) within a hinge pin 44. The gear 42, which is still engaged with the teeth 43 of the trigger 16, rotates backwards as the trigger 16 returns to the extended position, but the hub 40 remains stationary due to the internal one-way clutch. This operation may thus be repeated as necessary by additional actuations of the trigger 16, creating further tension in the tension member 36 until the predetermined amount of tension is achieved in the tension member 36 and enough pressure is applied between the barrel 14 and the leading element 32 to deform the crimp 28 that secures the tension member 36 (as shown in FIG. 12 and described above) or until the surgeon determines that enough tension has been applied to the tension member 36.

Figure 14:
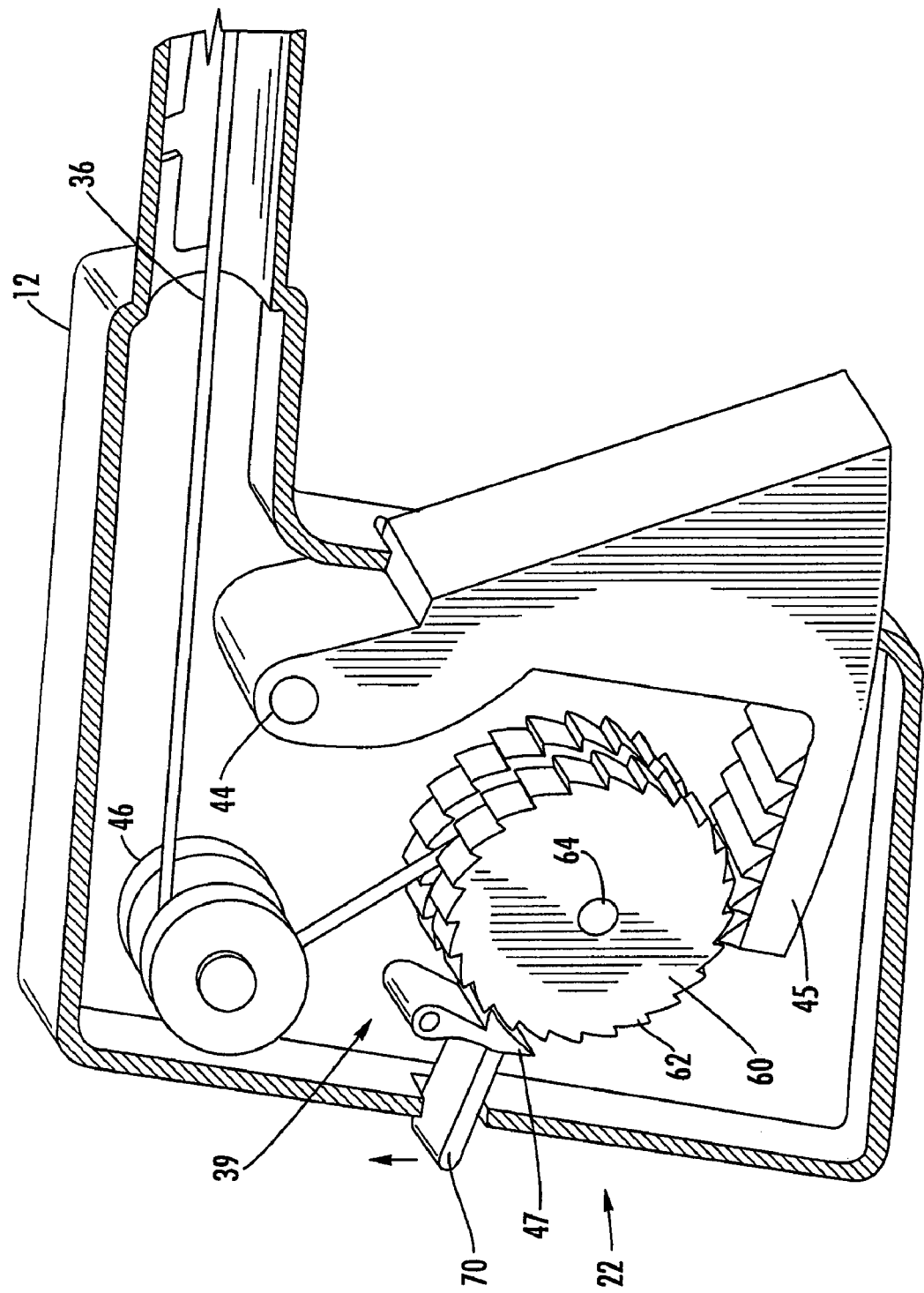
FIG. 14 is a section view of the casing and the grip portion of the tension member application device showing the tensioning mechanism according to another embodiment.

Referring to FIG. 14, another embodiment of the tensioning mechanism 39 is shown. In this embodiment, the tensioning mechanism 39 includes a gear 60 with teeth 62 that are designed for one-way engagement. In this way, when the trigger 16 is depressed, the gear 60 turns via engaging teeth 45 on the trigger 16 and winds the tension member 36 around a hub 64. When the trigger 16 is released, the biased hinge pin 44 returns the trigger 16 to the extended position, but the gear teeth 62 are no longer engaged with the teeth 45 of the trigger 16 due to the tapered configuration of the teeth 62, 45, for example, similar to a ratcheting mechanism. A gear pawl 47 may also be included to engage the gear teeth 62 when the trigger 16 is returning to the extended position (i.e., is not engaged with the gear teeth 62). The gear pawl 47 may include, for example, one tooth configured to allow the gear 60 to rotate when the gear teeth 62 are engaged with the teeth 45 of the trigger 16 and also configured to engage any one of the gear teeth 62 when the gear 60 is attempting to rotate in the opposite direction. In this way, the gear 60 is held stationary during the extension of the trigger 16 for subsequent actuation, and the tension created in the tension member 36 from previous trigger actuations may be maintained. These are two embodiments of how the tensioning mechanism 39 may be configured, but tensioning mechanisms other than those illustrated here may be employed.

Once the desired amount of tension in the tension member 36 is achieved and the terminal element 29 is attached, the length of the tension member 36 extending between the leading element 32 and the terminal element 29 may be detached from the tension member application device 10, as shown in FIG. 2B. Referring to FIG. 15, the slot 58 of the crimp 28 may include a sharp edge 72 which, upon deformation of the crimp 28, severs the tension member 36 (as shown in FIG. 16), thereby detaching the tension member application device 10 from the tensioned tension member 36. In other embodiments, such as the embodiment shown in FIGS. 17 and 18, the terminal element may include a crimp 80 having a scoring edge 88 configured to sever or at least score the tension member such that it may be severed, as previously described.

Another embodiment for detaching the tension member application device 10 from the tensioned tension member 36 may include a tension member release mechanism 70, as shown in FIG. 14. When the tension member 36 has reached the predetermined tension level that deforms the crimp 28 and attaches the crimp 28 to the tension member 36, the tension member release mechanism 70 may be pressed to disengage the pawl 47 from the gear teeth 62, thereby allowing free rotation of the gear 60. The tension member application device may then be drawn away from the terminal element 29 as the tension member 36 is unwound from the gear hub 64, such that the user may cut the tension member 36 proximate the terminal element 29 using any appropriate device.

In other embodiments, a method of using a tension member application device to install a tension member for stabilizing a bone is provided. Referring to FIGS. 1 and 2A, in one embodiment, the surgeon initially inserts the barrel 14 of the device 10 into a hole 15 drilled across a bone fracture 21 until the distal end of the barrel 14 is beyond the distal cortex 13 of the bone 17. The surgeon then pulls the barrel 14 along the first locking slots 50, towards the grip portion 22, via the barrel handles 24 to release the leading element 32 on the distal side of the bone and to lock the inner and outer chambers 30, 34 together (shown in FIGS. 3-6). The surgeon then rotates the barrel 14 by rotating the barrel handles 24 until they are inline with the longitudinal slots 20. The surgeon continues to retract the barrel 14 from the bone by pulling the barrel handles 24 towards the grip portion 22 until the handles 24 reach the ends of the longitudinal slots 54.

In other embodiments, as described above in conjunction with FIGS. 19A and 19B, the surgeon may apply tension to the tension member after inserting the barrel 14 and leading element 32 beyond the distal cortex. As tension is applied, the leading element 32 may engage the distal cortex by drawing the distal end of the leading element 32 towards the proximal end and bending the flat members 96 outwards, as shown in FIG. 19B. Once the width of the leading element 32 is thus expanded to engage the distal cortex, the surgeon may retract the barrel from the hole and proceed to attach the terminal element to the tension member 36 by applying tension to the tension member 36 until the predetermined amount of tension is achieved.

At this point, in some embodiments, the crimp eject mechanism 18 may be pressed or otherwise actuated to position the crimp 28 over the tension member 36 (shown in FIGS. 10-12). The barrel 14 may then be moved towards the crimp 28 and rotated by rotating the barrel handles 24 into the transverse locking slots 52, thereby pushing the crimp 28 into engagement with the static washer 26 to detach the static washer 26 from the casing 12 and form the terminal element 29 (shown in FIG. 2B after installation of the tension member 36). The surgeon may then actuate the trigger 16 to apply tension to the tension member 36 until the proper tension is achieved. As tension is applied to the tension member 36, the crimp 28 deforms to hold the tensioned tension member 36 in place.

In some cases, when the predetermined amount of tension on the tension member 36 is achieved, the crimp may sever the tension member 36. Alternatively, the crimp may score the tension member 36, and the surgeon may sever the tension member 36 by twisting or otherwise applying force to the tension member 36. In other cases, a tension member release mechanism 70 (shown in FIG. 14) may be actuated to release the tension on the tension member 36 between the terminal element 29 and the tension member application device 10 and provide slack in the tension member 36. As a result, the surgeon may then cut the tension member 36 proximate the terminal element 29 using any appropriate cutting tool. In some embodiments, the tension member application device is configured for a single use, such that the surgeon may dispose of the tension member application device after severing the installed tension member from the application device. In this way, there is no need to sterilize the device for subsequent tension member installations, and the risk of contamination in other patients may be reduced.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A device for stabilizing a bone comprising:
   a barrel configured to be inserted in a hole drilled bicortically through the bone;
   a tension member housed at least partially within the barrel and having a leading end;
   a leading element attached to the leading end of the tension member, wherein the leading element is configured to pass through the hole and to engage a distal cortex of the bone;
   a terminal element configured to attach to a trailing portion of the tension member while the tension member is at least partially disposed within the barrel and configured to engage a proximal cortex of the bone; and
   a tensioning mechanism configured to apply tension to the tension member, such that the terminal element attaches to the tension member at a predetermined tension of the tension member,
   wherein a length of the tension member extending between the leading element and the terminal element is configured to apply compression to the bone.

2. The device of claim 1, wherein the barrel comprises an outer chamber and an inner chamber, wherein the outer chamber at least partially surrounds the inner chamber and the outer chamber is configured to slide over and lock onto the inner chamber, thereby releasing the leading element from the barrel.

3. The device of claim 2, wherein the leading element comprises a body and a plurality of wings attached to the body, wherein the wings have a first position in which the wings are collapsed to allow the leading element to fit within the outer chamber and a second position in which the wings are expanded to increase a width of the leading element and permit engagement with the distal cortex.

4. The device of claim 3, wherein the wings are configured to be generally perpendicular to the tension member when in the second position, and wherein the wings are configured to move from the first position to the second position when unrestrained by the outer chamber.

5. The device of claim 1, wherein the leading element comprises a distal end, a proximal end, and at least one flat member connecting the distal and proximal ends, wherein each flat member is configured to bend outward and expand a width of the leading element to engage the distal cortex when the distal end is drawn toward the proximal end via the tension member.

6. The device of claim 1 further comprising a casing at least partially housing the barrel and configured to allow the barrel to move longitudinally within the casing.

7. The device of claim 6, wherein the terminal element comprises a static washer removably attached to an end of the casing and a crimp, wherein the static washer is configured to receive the crimp and wherein the crimp is configured to attach to the tension member and to engage the static washer.

8. The device of claim 7, wherein the static washer and crimp are configured with a taper and wherein the crimp is configured to collapse around the tension member when axially loaded under tension via the tension member.

9. The device of claim 7, wherein the crimp defines a slot extending from an edge of the crimp towards a center of the crimp, and wherein the slot is configured to receive the tension member.

10. The device of claim 7, wherein the crimp is configured to deform to attach to the tension member.

11. The device of claim 7, wherein the crimp comprises a scoring edge configured to score the tension member.

12. The device of claim 1, wherein the tensioning mechanism includes a trigger configured to apply tension to the tension member.

13. The device of claim 12, wherein the tensioning mechanism further comprises at least one gear configured to interact with the trigger and the tension member and to apply tension to the tension member upon actuation of the trigger.

14. The device of claim 1, wherein the terminal element comprises a cutter configured to cut the tension member proximate the terminal element such that the length of the tension member extending between the leading element and the terminal element is detached from the device.

15. A method of installing a tension member for stabilizing a bone comprising:
   inserting a barrel into a hole drilled in the bone such that an end of the barrel extends beyond a distal cortex of the bone, wherein the barrel at least partially houses the tension member and a leading element is attached to a leading end of the tension member;
   engaging the leading element with the distal cortex;
   withdrawing the barrel from the hole; and
   applying tension to the tension member to attach a terminal element to a trailing portion of the tension member, wherein the terminal element is configured to attach to the tension member while the tension member is at least partially disposed within the barrel and engage a proximal cortex of the bone when a predetermined amount of tension on the tension member is achieved.

16. The method of claim 15, wherein engaging the leading element with the distal cortex comprises moving an outer chamber of the barrel over an inner chamber of the barrel such that the outer chamber releases the leading element and locks onto the inner chamber.

17. The method of claim 15, wherein engaging the leading element with the distal cortex comprises applying tension to the tension member to draw a distal end of the leading element toward a proximal end of the leading element, thereby expanding the leading element.

18. The method of claim 15, wherein applying tension comprises attaching a crimp to the trailing portion of the tension member when the predetermined amount of tension is achieved, wherein the crimp is configured to engage a static washer to form the terminal element.

19. The method of claim 18, wherein applying tension comprises deforming the crimp when the predetermined amount of tension is achieved to attach the crimp to the tension member.

20. The method of claim 15, wherein applying tension comprises actuating a trigger to incrementally increase the tension in the tension member.

21. The method of claim 15 further comprising cutting the tension member proximate the terminal element.

22. The method of claim 21, wherein cutting the tension member comprises deforming at least part of the terminal element to score the tension member and applying force to the tension member to sever the tension member.

23. The method of claim 15, wherein applying tension comprises cutting the tension member proximate the terminal element.

\* \* \* \* \*